(12) United States Patent
Liang et al.

(10) Patent No.: US 11,666,879 B2
(45) Date of Patent: Jun. 6, 2023

(54) SMALL CHANNEL SHORT FIXED BED ADIABATIC REACTOR FOR OXIDATIVE COUPLING OF METHANE

(71) Applicant: SABIC GLOBAL TECHNOLOGIES B.V., Bergen op Zoom (NL)

(72) Inventors: Wugeng Liang, Sugar Land, TX (US); Sagar Sarsani, Sugar Land, TX (US); David West, Sugar Land, TX (US); James Kauffman, Sugar Land, TX (US); Jonathan Banke, Sugar Land, TX (US); Hector Perez, Sugar Land, TX (US); Robert C. Schucker, Sugar Land, TX (US); Tian Gu, Sugar Land, TX (US); Vemuri Balakotaiah, Houston, TX (US)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 61 days.

(21) Appl. No.: 16/981,444

(22) PCT Filed: Apr. 18, 2019

(86) PCT No.: PCT/US2019/028118
§ 371 (c)(1),
(2) Date: Sep. 16, 2020

(87) PCT Pub. No.: WO2019/204600
PCT Pub. Date: Oct. 24, 2019

(65) Prior Publication Data
US 2021/0031161 A1    Feb. 4, 2021

Related U.S. Application Data

(60) Provisional application No. 62/659,348, filed on Apr. 18, 2018.

(51) Int. Cl.
*B01J 8/02* (2006.01)
*C07C 2/84* (2006.01)

(52) U.S. Cl.
CPC ........... *B01J 8/0278* (2013.01); *B01J 8/0285* (2013.01); *C07C 2/84* (2013.01);
(Continued)

(58) Field of Classification Search
CPC ............... B01J 8/0278; B01J 8/0285; B01J 2208/00115; B01J 2208/022;
(Continued)

(56) References Cited

U.S. PATENT DOCUMENTS

| | | | |
|---|---|---|---|
| 4,128,595 A | | 12/1978 | Montgomery |
| 4,822,944 A | * | 4/1989 | Brazdil, Jr .................. B01J 8/02 585/310 |

(Continued)

FOREIGN PATENT DOCUMENTS

| | | |
|---|---|---|
| AU | 2013355038 A1 | 6/2014 |
| EP | 0962422 A1 | 12/1999 |

(Continued)

OTHER PUBLICATIONS

Arndt et al.; "Mn—Na2WO4/SiO2 as catalyst for the oxidative coupling of methane. What is really known?"; Applied Catalysis A: General; vol. 425-426; May 2012; p. 53-61; (abstract only).

(Continued)

*Primary Examiner* — Ali Z Fadhel
(74) *Attorney, Agent, or Firm* — Womble Bond Dickinson (US) LLP

(57) ABSTRACT

Disclosed herein are systems and processes for the conversion of a methane feedstock to $C_{2+}$ hydrocarbons.

17 Claims, 3 Drawing Sheets

(52) U.S. Cl.
CPC ...... *B01J 2208/00115* (2013.01); *B01J 2208/022* (2013.01); *C07C 2523/10* (2013.01)

(58) Field of Classification Search
CPC .... B01J 2208/00168; B01J 2208/00495; B01J 2208/00522; B01J 2208/0053; B01J 2208/021; B01J 2219/0204; B01J 8/06; B01J 19/2425; B01J 8/0242; C07C 2/84; C07C 2523/10
See application file for complete search history.

(56) References Cited

U.S. PATENT DOCUMENTS

| | | | | |
|---|---|---|---|---|
| 4,876,409 | A | * | 10/1989 | Leyshon .................. C07C 2/84 585/656 |
| 4,973,777 | A | * | 11/1990 | Alagy .................. B01J 19/2425 585/539 |
| 5,789,644 | A | | 8/1998 | Passler et al. |
| 5,824,834 | A | | 10/1998 | Bachtler et al. |
| 6,087,545 | A | | 7/2000 | Choudhary et al. |
| 6,139,810 | A | * | 10/2000 | Gottzmann .......... B01J 19/2475 422/240 |
| 8,013,196 | B2 | | 9/2011 | Mamedov et al. |
| 8,080,697 | B2 | | 12/2011 | Lin et al. |
| 8,119,554 | B2 | | 2/2012 | Kashani-Shirazi et al. |
| 8,815,080 | B2 | | 8/2014 | Sundaram |
| 9,352,295 | B2 | | 5/2016 | Rafique et al. |
| 2005/0048658 | A1 | | 3/2005 | Johnson et al. |
| 2005/0049445 | A1 | | 3/2005 | Johnson et al. |
| 2013/0165728 | A1 | | 6/2013 | Zurcher et al. |
| 2014/0073828 | A1 | | 3/2014 | Lange De Oliveira et al. |
| 2014/0107385 | A1 | * | 4/2014 | Schammel .............. B01J 8/001 585/501 |
| 2014/0128484 | A1 | * | 5/2014 | Hassan ................... C10G 2/33 502/200 |
| 2014/0128485 | A1 | * | 5/2014 | Hassan ................. B01J 12/007 422/162 |
| 2015/0065767 | A1 | * | 3/2015 | Henao ..................... C07C 2/84 585/300 |
| 2015/0152025 | A1 | * | 6/2015 | Cizeron .................. C07C 2/78 585/324 |
| 2015/0321974 | A1 | | 11/2015 | Schammel et al. |
| 2015/0329439 | A1 | | 11/2015 | Nyce et al. |
| 2019/0169089 | A1 | * | 6/2019 | Cizeron ................... C07C 2/84 |

FOREIGN PATENT DOCUMENTS

| | | |
|---|---|---|
| WO | WO 2004/103936 A1 | 12/2004 |
| WO | WO 2013/050764 A1 | 4/2013 |
| WO | WO 2013/121230 A1 | 8/2013 |
| WO | WO 2013/177433 A2 | 11/2013 |
| WO | WO 2015/057753 A1 | 4/2015 |
| WO | WO 2015/081122 A2 | 6/2015 |
| WO | WO 2016/097045 A1 | 6/2016 |

OTHER PUBLICATIONS

Sinev et al.; "Kinetics of oxidative coupling of methane: Bridging the gap between comprehension and description"; Journal of Natural Gas Chemistry; vol. 18; Sep. 2009; p. 273-287 (abstract only).
D.W. Leyshon; "Thin Bed Reactor for Conversion of Methane to Higher Hydrocarbons"; Natural Gas Conversion; 1991; p. 497-507.
Capel et al.; "Design and additive manufacture for flow chemistry"; Lab on a Chip; vol. 13; 2013; p. 4583-4590.
Levin, Michael; "How to Scale Up Scientifically"; Pharmaceutical Technology; vol. 26; 2005; 8 pages.
Wozny et al.; "Oxidative Coupling of Methane: A Design of Integrated Catalytic processes"; Chemical Engineering Transactions; vol. 21; 2010; p. 1399-1404.
Pak et al.; "Elementary Reactions in the Oxidative Coupling of Methane over Mn/Na2WO4/SiO2 and Mn/Na2WO4/MgO Catalysts"; Journal of Catalysis; vol. 179; 1998; p. 222-230.
International Patent Application No. PCT/US2019/028118; Int'l Search Report and the Written Opinion; dated Jul. 17, 2019; 14 pages.

\* cited by examiner

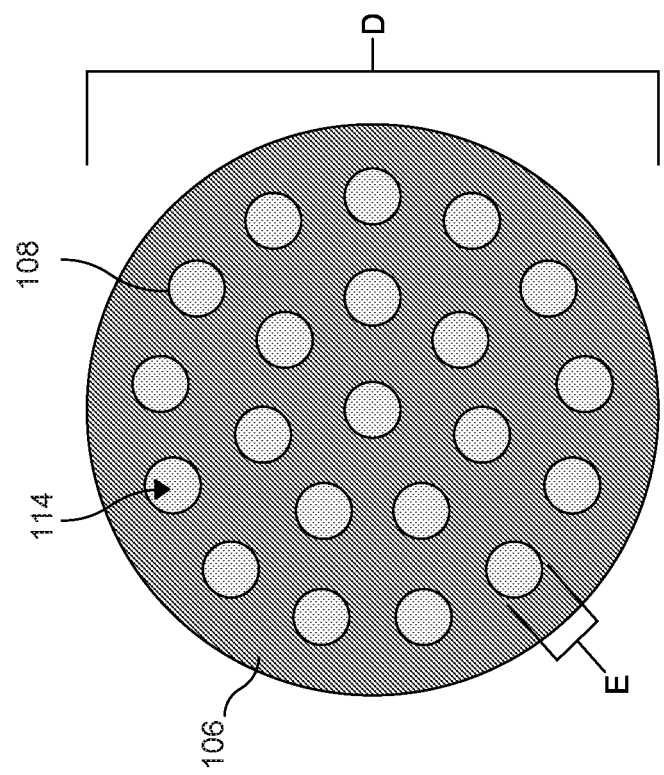
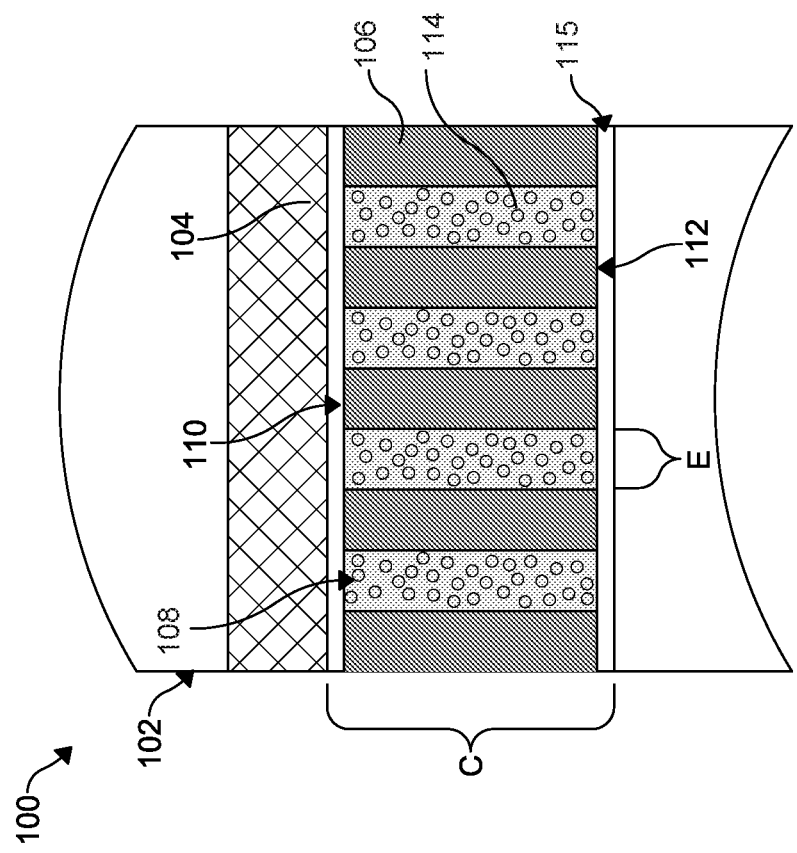

SMALL CHANNEL SHORT FIXED BED ADIABATIC REACTOR FOR OXIDATIVE COUPLING OF METHANE

CROSS-REFERENCE TO RELATED APPLICATION

This application is the National Stage of International Application No. PCT/US2019/028118 filed Apr. 18, 2019, which claims the benefit of U.S. Provisional Application No. 62/659,348 filed Apr. 18, 2018, the disclosures of which are incorporated herein by this reference in their entireties.

TECHNICAL FIELD

The present disclosure relates to systems and apparatuses for the conversion of hydrocarbons to C2 hydrocarbons. More specifically, the disclosure relates to tubular fixed bed reactors for the conversion of methane.

BACKGROUND

The conversion of methane to higher molecular weight hydrocarbons ($C_{2+}$ hydrocarbons) in the presence of an appropriate catalyst may take place effectively at elevated temperatures in the range of about 500° C. to about 1200° C. The conversion reactions may be exothermic, and may be strongly exothermic, accompanied by considerable amounts of heat energy. To properly regulate the reaction and to prevent excessive undesirable side reactions, the exothermic heat of reaction may be removed. Conventionally, heat removal, using a heat removal agent or medium, may lower the temperature of the reaction reactants and products and avoid excessive temperature increases in the reactor.

In an example, the oxidative coupling of methane (OCM), a highly exothermic process, presents many challenges for reactors and catalysts designs. Because methane is a very stable compound, a special catalyst is required for activation at certain temperatures to form methyl radicals. In addition to the coupling reaction of methyl radicals to form the desired coupling products (for example, C2 products), the methyl radicals react with gas phase oxygen or lattice oxygen on the catalyst surface to form oxygen containing compounds. These oxygen containing compounds are transformed to deep oxidation products, carbon monoxide CO and carbon dioxide $CO_2$, which may lower the reaction selectivity. The reactions between methyl radicals and oxygen may be reduced by increasing the reaction temperature, for example, to temperatures at or above 600° C. As noted, the OCM reaction is an exothermic reaction releasing considerable amounts of heat during the reaction. With the reaction heat produced, the catalyst bed temperature may be much higher than needed, for example, higher than 1000° C. At elevated temperatures, reaction selectivity is reduced due to deep oxidation of products formed or due to reforming reaction. To regulate the temperature, a heat removal agent may be used, however, many of these agents may not be able to operate at elevated temperatures of the OCM reaction. And, heat removal agents that are viable at the OCM reaction temperatures may be prohibitively expensive.

Other concerns arise regarding the conventional OCM catalyst. With the traditional OCM catalysts, due to their relative low productivity, a large amount of catalyst may be needed to achieve the required production and the typical catalyst bed is long in length. With the required feed flowrate, to reduce the pressure drop across the catalyst bed, a large catalyst particle size is typically used. For the OCM reaction however, a large catalyst particle size results in mass transfer resistance. The mass transfer resistance may negatively affect the catalyst performance (reduces catalyst activity). Moreover, the temperature rises within the catalyst particle which also lowers catalyst performance.

Therefore, there is a strong need to develop a reactor system and a high performance catalyst to achieve an economical and efficient OCM process.

SUMMARY

As described in more detail herein, the present disclosure provides a reactor system for an oxidative conversion of methane comprising: a reactor vessel having a reactant inlet and a product outlet; a pre-heating component disposed within the reactor vessel configured to receive feedstock from the reactant inlet; and one or more reactor bodies configured to receive the feedstock from the reactant inlet via the pre-heating component, each reactor body having a plurality of channels extending there through, wherein the channels are configured to receive a catalyst.

The present disclosure further relates to a fixed bed reactor comprising: a reactor body having a plurality of channels extending there through, wherein the channels extend through from a first surface of the reactor body to a second surface of the reactor body, wherein the channels are about parallel to one another, and wherein the channel has a diameter of less than about 10 (millimeter) mm, wherein the reactor body has a height of about 300 mm, wherein the channels are configured to receive a catalyst, wherein the catalyst has a particle size less than from about $¼^{th}$ to about $½0^{th}$ the diameter of the a channel; and one or more walls disposed adjacent the first surface and the second surface configured to maintain the catalyst within the channels. In one aspect, a method of the present disclosure may comprise contacting the hydrocarbon feedstock and an oxidant with a catalyst in a reactor system, wherein the reactor system comprises: a reactor vessel having at least a reactant inlet and at least a product outlet; one or more reactor bodies configured to receive the hydrocarbon feedstock and oxidant from the reactant inlet, each reactor body having a plurality of channels extending there through, wherein the channels extend through from a first surface of the reactor body to a second surface of the reactor body, wherein the channels are configured to receive the catalyst, wherein the channels have a diameter, and wherein the catalyst has a particle size about from about $¼^{th}$ to about $½0^{th}$ of the size of the diameter of a channel; and one or more walls disposed adjacent one or more of the first surface and the second surface, wherein the walls are configured to maintain the catalyst within the channels, at reaction conditions to provide a hydrocarbon reaction product.

BRIEF DESCRIPTION OF THE DRAWINGS

The above-mentioned and other features and advantages of this disclosure, and the manner of attaining them, will become apparent and be better understood by reference to the following description of an aspect of the disclosure in conjunction with the accompanying drawings, wherein:

FIG. 1 shows a diagram for a reactor system of a fixed bed reactor according to aspects of the present disclosure.

FIG. 2 shows a top view of a reactor body according to the present disclosure.

Figure 3:
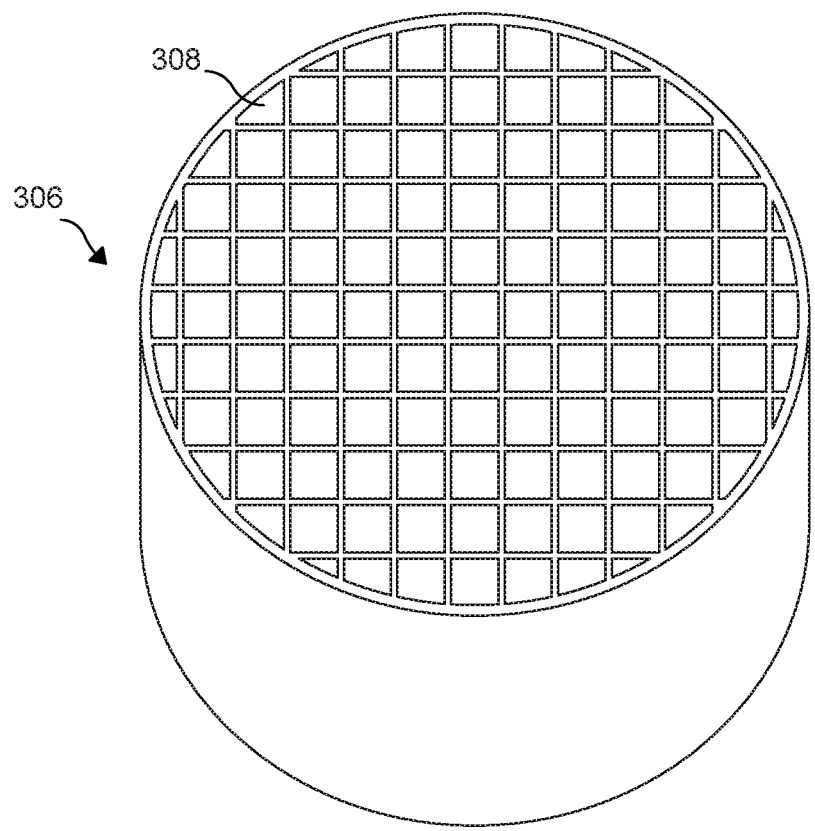
FIG. 3 shows a cross section of a 60-cell silicon carbide monolith reactor body having 2 mm by 2 mm cell dimensions according to aspects of the present disclosure.

Additional advantages of the disclosure will be set forth in part in the description which follows, and in part will be obvious from the description, or can be learned by practice of the disclosure. The advantages of the disclosure will be realized and attained by means of the elements and combinations particularly pointed out in the appended claims.

DETAILED DESCRIPTION

As a highly exothermic process (for example, about −67 kilocalories per mole, kcal/mol), an oxidative coupling of methane (OCM) may be performed in a fixed bed reactor, such as a tubular fixed bed reactor. Fixed bed reactors have been considered for use in high energy reactions including those that are highly exothermic, for example, (partial) oxidation or hydrogenation, or highly endothermic, for example, steam reforming. Conventionally, a fixed bed reactor may comprise a tubular or massive bed configuration where the bed exploits indirect heat exchange properties to carry out the energetic reactions. In a catalytic fixed bed reactor, reactions generally occur on the surface of a catalyst arranged in the so-called fixed bed of the reactor. Indirect heat exchanges occur via a circulating heat transfer medium thereby regulating temperature sensitive and highly exothermic reactions. However, the conventional reactor systems may be less advantageous because of their associated costs, undesirable pressure drop across the reactor system, and complications of heat removal and product degradation. The disclosed reactor system combines unique features of heat management, reactor design, and a high activity catalyst to overcome the disadvantages of a fixed bed reactor for OCM described herein.

For a conventional tubular fixed bed reactor, physical reactor system demands including heat transfer efficiency and a low pressure drop may be in conflict with chemical demands such as gas contact efficiency (or the contacting of the gaseous reagents). For example, heat of reaction generated at the catalyst within the reactor tubes may be transferred to the reactor body comprising the tubes and any temperature regulating medium disposed within the reactor. Generally, the goal of a heat transfer cycle within the reactor system may be to maintain the temperature in the fixed bed within a specific range to avoid, for example, a deep oxidation reactions. Poor heat transfer efficiency may also result in radial temperature gradients within the tubes of the reactor system. That is, hot spots may occur towards the center of tubes where less heat transfer may occur. Reaction conditions of an OCM process, such as the temperature profile between greater than 500° C. to about 1200° C., or more specifically, from about 700° C. to about 950° C., may preclude efficient heat transfer because conventional media may not have the capacity to transfer heat from the reaction site.

In addition to the described heat transfer properties, a conventional multi-tubular fixed bed reactor may also be subject to pressure drop over the reactor tubes. This pressure drop may be even more apparent where the catalyst particles are particularly small and reactor tubes are relatively long. The pressure across tubes may drop within a given reactor system in an amount between 2 bar and 20 bar, very often, between 5 bar and 10 bar. As a general caveat, the smaller the catalyst particles, the higher the $C_{2+}$ selectivity, but, smaller particles are more likely to result in a pressure drop across the reactor tubes as described above. Minimizing the pressure drop over the reactor would thus improve the capital investment in the reactor system. A reduced pressure drop requires less investment because, for example, a smaller compressor may be used and the pressure requirements of equipment used to regulate pressure in the reactor system may be less rigorous and thus reduce operational costs since less energy is required.

The traditional reactor system for OCM has a few disadvantages with respect to the catalyst as well. As described above, limited heat transfer performance makes local runaways (hotspots) more likely, which may result in lower performance and local deactivation of the catalyst. To avoid deep oxidation reactions, the maximum temperature within the reactor system is regulated. However, the presence of temperature gradients within the reactor may result in at least a portion of catalyst operating at sub-optimal conditions. In addition to the radial temperature difference, there may also be an axial temperature profile which may exacerbate the catalyst performing at sub-optimal levels. The use of high-activity catalyst also requires relatively small catalyst particles in order to obtain the desired $C_{2+}$ selectivity. Such particles may result in very high pressure drops over the catalyst bed also as described above. These high pressure drops require large (expensive) compressors, and add a substantial power requirement to the operation of an OCM plant. Moreover, if the catalyst bed temperature is, for example, higher than 950° C., thermal reactions, such as reforming, may start to occur and will lower the selectivity. Conventionally, heat removal agents, such as molten salts, may be applied outside of the reactor tube to control the temperature in the catalyst bed. To find a molten salt to be able to operate at such high temperature may be very difficult if not impossible. In addition, the cost for reactor for such high temperature operation may be very high and thus not economically viable.

With the traditional OCM catalysts, due to their relative low productivity, a large amount of catalyst may be needed to achieve the required production and the typical catalyst bed is long in length. With the required feed flowrate, to reduce the pressure drop across the catalyst bed, a large catalyst particle size is used. For the OCM reaction however, a large catalyst particle size results in mass transfer resistance. The mass transfer resistance may negatively affect the catalyst performance (reduces catalyst activity). Moreover, the temperature rises within the catalyst particle which also lowers catalyst performance. Systems and methods of the present disclosure combine fixed reactors and certain catalysts to overcome concerns of conventional fixed bed reactors for at least OCM reactions.

The reactor system of the present disclosure addresses at least the foregoing concerns. The disclosed reactor combines a unique heat management system with a shorter reactor dimension and high activity catalyst to alleviate the disadvantages of a conventional fixed bed reactor for OCM processes. Specifically, the reactor may alleviate system stress attributed to limited heat transfer efficiency and pressure drops while incorporating a high activity catalyst, thereby providing an improved selectivity for hydrocarbon.

The disclosed reactor system improves heat transfer efficiency while also minimizing pressure drops across the reactor system by exploiting certain dimensions of the fixed bed reactor as well as properties of the desired catalyst. The disclosed reactor system may comprise a reactor vessel having a pre-heat section and one or more reactor bodies therein. Each reactor body comprises a plurality of channels that extend there through. Each channel of the plurality of channels may be packed with an active catalyst. The pre-heat section is configured to receive heat from the exothermic OCM reaction occurring within the one or more reactor bodies. The pre-heat section may comprise a high heat conductive medium. The feedstream enters the reactor vessel and traverses the pre-heat section wherein the absorbed heat from the OCM reaction heats the incoming feedstream. The reactor body, channels, and catalyst particles may each have particular size or dimensions to achieve the highly selective conversion of the heated feedstream.

The disclosed reactor system may operate adiabatically. With the adiabatic operation, under steady operation conditions, no external heat removal is needed. The present disclosure relates to the adiabatic operation of the fixed bed reactor with the feed inlet temperature to the reactor at near ambient temperature, so that no expensive heat exchanger is needed to heat up the feed. Moreover, the present disclosure relates to high performance catalysts. With the high performance catalysts, to achieve the required production, much less amount of catalyst is needed, so that a much shorter catalyst bed is required. With the much shorter catalyst bed, smaller catalyst particles can be used without resulting in high pressure drop across the catalyst bed. Smaller particle size will reduce the mass and heat transfer resistances within the particle, so that the high performance of the catalyst can be maintained. With the smaller particle size of the catalyst, small channel will be used as described in front. The small channel used will enhance the heat transfer in radial direction, so that the temperature rise in the radial direction will be reduced, which will benefit the performance of the OCM reaction. With the high performance catalyst, smaller catalyst particle size, small channels and low pressure drop cross the bed, the performance of the new reactor system is improved.

FIG. 1 presents an exemplary reactor system 100 where FIG. 1 shows a cross-sectional side view of a reactor vessel 102 having an inlet and an outlet where the inlet is configured to receive a feedstream. The reactor vessel may comprise a pre-heat section 104 and reactor body 106. The pre-heat section 104 is configured to be adjacent the reactor body 106 such that as a feedstream enters the reactor vessel 102, it traverses the pre-heat section 104 and enters the reactor body 106.

The reactor vessel 102 may comprise an inert material. Exemplary materials may include, but not limited to, refractory materials, such as alumina, silica or zirconia. The reactor vessel 102 may comprise of steel or stainless steel. When the reactor vessel 102 comprises steel or stainless steel, an interior surface of the reactor vessel 102 may comprise an inert coating. The reactor vessel 102 may have a particular shape and dimension, but is not limited to the shapes or geometries disclosed or provided as examples herein. In various aspects, the reactor vessel 102 may be cylindrical as presented in FIG. 1.

The reactor body 106 may comprise a plurality of channels 108 there through such that the channels extend from a first surface 110 of a reactor body 106 to a second surface 112 of the reactor body 106. Each channel 108 of the reactor body 106 is configured to receive a catalyst 114. Thus, channels 108 of the reactor body 106 may correspond to the tubes of the fixed bed reactor described herein. Each channel 108 may have a diameter E and each channel 108 extends the distance or height C of the reactor body 106 such that a channel length and the height C of the reactor body 106 may be the same.

The reactor body 106 may have a particular shape and dimension, but is not limited to the shapes or geometries disclosed or provided as examples herein. In various aspects, the reactor body 106 may be cylindrical as presented in FIGS. 1 and 2. For a cylindrical reactor body 106, each channel 108 may originate at a first surface, or a first planar surface, 110 of the reactor body 106 and end at a second surface, or a second planar surface, 112 of the reactor body 106.

The reactor body 106 according to the present disclosure may have a particular size. In various examples, the reactor body 106 may have a size of 20 millimeters (mm) or greater. Across with respect to the reactor body may refer to the width across which the channels are disposed, rather than the height of reactor body which the channels may be said to traverse. In a specific example, the reactor body 106 may have diameter D of 20 mm or greater where the reactor body is cylindrical. The reactor body may have a height C of from about 10 mm to 300 mm. Generally, C may be no greater than 300 mm.

The reactor body may be comprised of a sufficiently inert material, that is, a material that may not readily react with the reagents or catalyst even at elevated temperatures (those between 500° C. and 1200° C. for OCM). Materials for the reactor body may also comprise materials having a thermal conductivity of at least about 2 Watts per meter Kelvin (W/m·K) so as to provide sufficient heat transfer of the heat generated during the OCM process. In further examples, the reactor body may comprise a material having a thermal conductivity of at least about 10 W/m·K, or at least about 20 W/m·K, or at least about 40 W/m·K. Exemplary materials may include, but are not limited to silicon carbide, quartz, a metal coated with inert materials, or a combination thereof. In a specific example, the reactor body 106 comprises silica carbide.

In some examples, channels 108 of the reactor body may extend through the reactor body 106 in parallel. The channels 108 may be tubular and may be coterminous such that each of the channels 108 begins at the first surface 110 of a reactor body 106 and ends at the second surface 112 of the reactor body 106. Channels 108 of the reactor body 106 may have a particular size so as to exploit an optimal heat transfer efficiency throughout the reactor body 106 during a methane conversion process, or other energetic reaction. A channel 108 of the plurality of channels has a length no greater than about 300 mm. Each channel 108 may have a channel size, for example, a diameter E of less than about 10 mm. In specific examples, each channel may have a size, or a diameter E, of about 5 mm. The channels 108 may be spaced uniformly through the reactor body 106 as shown in FIGS. 1 and 2. In some examples however, the channels may be randomly spaced.

A channel of the present disclosure may have a particular shape and dimension. As disclosed according to the present disclosure, the channel may have a circular or round shape and thus its size may be characterized as a diameter. However, the disclosed channel may have any appropriate shape allowing for receipt of the catalyst particles including, for example, hexagonal, square, round, oblong, or star. For example, FIG. 3 shows a reactor body 306 having channels 308 with a square shape.

Referring again to FIG. 1, an appropriate catalyst 114 may be disposed within the plurality of channels 108 of the reactor body 106. The catalyst 114 may be disposed within the channels 108 in a particulate form. It is at a surface of the catalyst particles that the conversion reaction may occur within the reactor system. The catalyst particles may have a particular size. Specifically, the catalyst 114 may have a size of up to about 1/4th to about $1/20^{th}$, more specifically, about $1/10^{th}$ the size of the diameter E of a channel 108 of the reactor body 106. The catalyst may have a particle size of less than about 100 mesh or less than about 0.15 mm. In some examples, the catalyst has a particle size between about 80 mesh and 20 mesh, or between about 0.180 mm and 0.85 mm.

When the reactor body 106 is loaded with catalyst, the pre-heat section 104 adjacent the first surface 110 is loaded as shown in FIG. 1. The pre-section is used to heat up the feedstream to the required temperature. In certain aspects, the catalyst 114 may or may not fill the volume of an individual channel 108. For example, an area of a channel 108 may be empty.

While the heat transfer and pressure considerations are weighed, the disclosed reactor systems for methane conversion may require certain characteristics for the catalyst used to drive the reaction. In various aspects of the present disclosure, the activity of a given catalyst may contribute to the overall efficiency of the reactor system. An active catalyst may refer to a catalyst that facilitates the conversion reaction at temperatures between about 500° C. and 1200° C. The active catalyst may comprise a strontium-cerium-ytterbium oxide (Sr—Ce—Yb-oxide) or a strontium-lanthanum-neodymium-ytterbium oxide (Sr—La—Nd—Yb-oxide). High performance catalysts may be used in the disclosed reactor system so that a lower catalyst volume (corresponding to a shorter catalyst bed because of the shorter tubes) may be loaded in each channel. Less catalyst and the shorter tubes may provide a pressure drop cross the fixed catalyst bed of less than about 10 bar.

The catalyst systems which demonstrated such performance are catalysts containing Sr—Ce—Yb oxides, Sr—La—Nd—Yb-oxides, and other high performance catalyst systems. An active catalyst as described herein may demonstrate catalytic stability at reaction temperatures so that the catalyst may be less susceptible to degradation. For commercial viability of the disclosed reactor system, the catalyst may be stable, especially, be stable at the highest temperature of the catalyst bed. For example, the catalyst should be stable for 2 years or more, preferred be stable for 3 years or more, more preferred be stable for 4 years or more.

To retain the catalyst particles within the channels of the reactor body, one or more walls 115 may be disposed adjacent one or more of the surfaces 110, 112 of the reactor body 106. That is, the walls 115 may be disposed at ends of the channels 108 thereby keeping the catalyst 114 particles within the channels 108 of the reactor body 106. The walls 115 may comprise an inert material. The walls 115 may be thin and sufficiently resilient to withstand heat of the reactor system. The wall 115 may be a sheet or a film-like form configured to be disposed adjacent a surface of the reactor body. The wall 115 may be porous, however, the pores of the wall may be smaller than the size of the catalyst particles so as to retain the catalyst within the channels 108 of the reactor body 106. In some examples, the walls may have a thickness of a few millimeters (mm), for example, 2-3 mm. Suitable materials comprising the disclosed walls may include inert materials as well as materials that are able to withstand reaction temperatures of greater than about 500° C. Exemplary materials may include, but are not limited to, metal screens, quartz felt, ceramic foams, silicon carbide, alumina, and zirconia ceramic. In some examples, materials having a high thermal conductivity are preferred. Materials for the walls may comprise materials having a thermal conductivity of at least about 2 W/m·K, or of at least about 5 W/m·K, of at least about 10 W/m·K, or of at least about 20 W/m·K, or of at least about 40 W/m·K.

The disclosed reactor system may transfer the reaction heat produced during the reaction from the reactor body to the feedstream of the reactor by using the high thermal conductive pre-heat section 104. The feedstream, which is at a lower temperature, is heated up by the reactor body before reaching the catalyst bed. With this heat transfer strategy, the temperature rise in the catalyst bed of the reactor body is reduced. At the same time, the feed temperature is raised to a temperature such that the reaction forming deep oxidative products CO and $CO_2$ is limited. This lower temperature increase across the catalyst bed and the high feed temperature to the catalyst bed are both important to achieve a highly selective operation for the OCM reaction.

The disclosed reactor system allows for certain performance parameters. The high performance catalyst used can be operated at gas hour space velocity (GHSV) from 5,000 (1/hour, $hr^{-1}$) hr-1 to 1,000,000 hr-1, more preferred from 50,000 hr-1 to 500,000 hr-1, which is at least 10 times higher than traditional OCM catalysts. With such high GHSV, to produce the required amount of product, the catalyst loading can be much less. As such, aspects of the present disclosure enable the use of a shorter catalyst bed (here, up to 300 mm). With a short catalyst bed, the pressure drop across the catalyst bed will be much lower. This lower pressure drop allows for the use of a catalyst having a smaller particle size. Pressure drop across the catalyst bed is important for the OCM reaction. A high pressure drop will reduce the catalyst selectivity. With smaller catalyst particle size, a smaller diameter channel can be used. Smaller catalyst particle size reduces mass and heat transfer resistances within the catalyst particle. Smaller channel diameter may reduce catalyst bed radial direction heat transfer resistance. Thus, the configuration of the disclosed reactor system enables high performance.

With the high thermal conductivity reactor body, the heat produced from the reaction may be transferred to the front of the catalyst bed and to the pre-heat section 104 as shown in FIG. 1. The high thermal conductive medium in the pre-heat section 104 transfer heat from the reaction within the channels 108 to the feedstream. The feedstream is thereby heated from its inlet temperature before reaching the catalyst bed. The feed reactant inlet temperature before entering the pre-heat section 104 is at 400° C. or below, at 300° C. or below, at 250° C. or below.

The pre-heat section 104 may be loaded with high heat conductive inert materials. Suitable examples of conductive inert materials may include a silicon carbide, quartz, a metal coated with inert materials, or a combination thereof. The high heat conductive inert materials may be in the form of spheres, cylinders, hollow cylinders or other shapes. In the pre-heat section 104, the feedstream 107 will be heated up to the required temperature before reaching the catalyst bed (channels 108) of the reactor body 106. The pre-heat section 104 may be configured to heat the feedstream to a specific temperature before entering the catalyst bed. Heating may be achieved by the presence of a high heat conductive medium. This temperature may be selected to achieve high selectivity in the catalyst bed. The selected temperature may depend upon the catalyst used in the catalyst bed. The temperature may be at 500° C. or greater, or at 550° C. or greater, or at 600° C. or greater. The medium of the pre-heat section 104 should be inert to the reaction. The high heat conductive medium used in the pre-heat section 104 may include, but are not limited to, silicon carbide (SiC), quartz, metals coated with inert materials. The materials may be spheres, cylinders, hollow cylinders or other shapes. The pressure drop across the pre-heat section 104 is desirably low. The pressure drop across the pre-heat section 104 may be less than $\frac{1}{10}^{th}$ of that of the catalyst section, or less than $\frac{1}{20}^{th}$ of that of the catalyst section, or less than $\frac{1}{50}^{th}$ of that of the catalyst section.

After the feed enters the catalyst bed (channels 108 with catalyst 114 therein), the OCM reaction occurs. The catalyst bed will be designed to have high oxygen conversion when the feed mixture exits the catalyst bed. The oxygen conversion may be 80% or higher as reaction products exit the catalyst bed. In further examples, the oxygen conversion may be at 90% or higher, or at 95% or higher.

As described herein, the disclosed reactor system 100 may be operated adiabatically. That is, the temperature may rise within the reactor system with the increase of oxygen conversion. The catalyst bed (reactor body 106 and channels 108 therein) and reactor system operation conditions may be configured to have the highest temperature in the catalyst bed at or below a specific temperature. This temperature restriction may be used to ensure that thermal reactions, such as reforming, may be limited. The temperature of the reactor system may be limited to at or below 1,000° C., at or below 975° C., or at or below 950° C. The goal of the inlet temperature and the outlet temperature of the reactor designed above is to achieve the highest selectivity from the reaction based on the catalyst used in the catalyst bed.

In some aspects, the reactor system may comprise a plurality of reactor bodies, each reactor having a plurality of catalyst filled channels extending there through. The multiple reactor bodies disposed adjacent one another may form a reactor body layer. In yet further aspects, the reactor system may comprise a plurality of reactor body layers.

In various aspects, the present disclosure provides a reactor system for the conversion of a hydrocarbon feedstock comprising methane to $C_2$ hydrocarbons. An OCM reaction promotes the formation of alkene hydrocarbons such as ethylene using an exothermic reaction of methane and oxygen over one or more catalysts according to the following overall equation (1):

$$2CH_4 + O_2 \rightarrow C_2H_4 + 2H_2O \tag{1}$$

A method for converting a hydrocarbon feedstock to coupled hydrocarbon products comprising: contacting the hydrocarbon feedstock and an oxidant with a catalyst in a reactor system. In some examples, the feedstock may be pre-heated, which may require additional energy costs and heat resistant materials forming the reactor system. The reactor system may comprise a reaction vessel having at least a reactant inlet and at least a product outlet disposed therein for the receipt and exit of the feedstock and a formed product mixture. One or more reactor bodies configured to receive the hydrocarbon feedstock and oxidant from the reactant inlet may be disposed within the reactor vessel. Each reactor body may have a plurality of channels extending there through such that each of the channels extend through from a first surface of the reactor body to a second surface of the reactor body. Channels may be configured to receive a catalyst. Each channel may have a diameter and the received catalyst has a particle size that may be about $\frac{1}{4}^{th}$ to about $\frac{1}{20}^{th}$ of the size of the channel diameter. To retain the catalyst within the channel, one or more walls may be disposed adjacent one or more of the first surface and the second surface of the reactor body.

The reactor design of the present disclosure may be useful for large scale production of $C_{2+}$ hydrocarbon products via an OCM process. The disclosed dimensions and properties of the reactor bodies, channels, and catalyst described herein may be configured for commercial or industrial production.

Appropriate reactor systems may comprise a few of the disclosed reactor bodies having channels there through and active catalyst disposed within the channels in order to meet industrial OCM demands. For example, a given reactor system may have 5 reactor bodies. In further examples, a given reactor system may comprise about 3 reactor bodies. These reactor bodies may be configured as individual reactor bodies, each having its own feed system. After reaction, products obtained from each reactor body can be combined and sent to downstream sections for separation. These reactor bodies can also be configured as multi-stage beds with methane feed to the first stage of the bed and oxygen uniformly distributed to different stages. These reactor bodies can also be configured as a combination of a few independent multi-stage beds. The configuration of the reactor bodies may depend on the size of a given industrial plant and its OCM output for a given year.

In the reaction, methane ($CH_4$) may be activated heterogeneously on the catalyst surface, thereby forming free methyl radicals. The free radicals may then couple in the gas phase to form ethane ($C_2H_6$). The ethane may undergo dehydrogenation at the catalyst or in gas phase to form ethylene ($C_2H_4$).

As provided herein, the overall reaction may proceed according to formula (1) above. More specifically, however, the oxidative conversion of methane to C2 hydrocarbons may proceed through stoichiometric reactions of which can be described by the following equations (2-5):

$$2CH_4 + O_2 = C_2H_4 + H_2O \quad \Delta H = -34 \text{ kcal/mol} \tag{2}$$

$$2CH_4 + 1/2\ O_2 = C_2H_6 + H_2O \quad \Delta H = -21 \text{ kcal/mol} \tag{3}$$

$$CH_4 + 1.5O_2 = CO + 2H_2O \quad \Delta H = -124 \text{ kcal/mol} \tag{4}$$

$$CH_4 + 2O_2 = CO_2 + 2H_2O \quad \Delta H = -192 \text{ kcal/mol} \tag{5}$$

The overall reaction is exothermic (enthalpy, $\Delta H = -67$ kcal/mol) and historically has been conducted at very high temperatures of from about 750° C. to about 950° C. to provide a C2 (ethane+ethylene) yield reported to be in the range of 15%-25%.

A conventional OCM reaction comprises a catalytic gas phase reaction of methane and an oxidant, such as oxygen, to provide one or more hydrocarbons having two or more carbon atoms (which may be collectively referred to herein as coupling products). The OCM process may include a methane feedstream or source and an oxidant feedstream provided to one or more reactor vessels equipped for the OCM reaction.

The source of methane may comprise a commercial natural gas source, a natural gas feed from one or more municipal or industrial gas suppliers. In one example, at least a portion of the methane may comprise biogas, that is, methane that is derived from one or more processes involving the decay of organic substances. Or, at least a portion of the methane may be provided as a byproduct from another co-located process stream or another facility. In further examples, the methane source may comprise a liquefied natural gas ("LNG") or compressed natural gas ("CNG") terminal or storage facility. At least a portion of the methane may comprise wellhead natural gas drawn directly from a naturally occurring or manmade subterranean reservoir or from storage facilities fluidly coupled to the naturally occurring reservoir. The methane source may comprise a gas or mixture of gases containing at least about 5 mole percent (mol %) methane; at least about 10 mol % methane; at least about 20 mol % methane; at least about 30 mol % methane;

at least about 40 mol % methane; at least about 50 mol % methane; at least about 60 mol % methane; at least about 70 mol % methane; at least about 80 mol % methane; at least about 90 mol % methane; or at least about 95 mol % methane.

In various aspects of the present disclosure, methane may be reacted with an oxidant in the presence of a catalyst. As an example, a methane feed and an oxidant feed may be combined for contact with the active catalyst. An oxidant in the form of purified oxygen, for example may be supplied by an air separation unit ("ASU") equipped to the OCM reactor system. As provided herein, at least a portion of the oxidant may include nitrogen. The oxidant may further include small quantities of inert gases such as argon, particularly where air is used to provide a portion of or all of the oxidant. Nitrogen concentration in the oxidant may be dependent upon the one or more sources used to provide the oxidant, however the nitrogen may be present in the oxidant in an amount no more than about 5 mol %; no more than about 10 mol %; no more than about 20 mol %; no more than about 30 mol %; no more than about 40 mol %; no more than about 50 mol %; no more than about 60 mol %; or no more than about 70 mol %.

Processing conditions for the oxidative coupling of methane may depend upon a number of factors. For example, the net methane-to-oxygen ($CH_4/O_2$) ratio may affect conditions. The methane and oxidant may be provided in a specific ratio in the OCM reactant mixture for the OCM process. The methane-to-oxygen stoichiometric ratio may also affect the overall conversion of raw materials to one or more preferred products in the OCM product mixture such as the desired coupling products. Where oxygen as the oxidant is the limiting reagent (i.e., maintaining a stoichiometric ratio for methane molar concentration to oxygen molar concentration of greater than 2:1) the likelihood of a detonation or deflagration occurring within the one or more reaction vessels may be reduced. In at least some aspects, where the methane is the limiting reagent, the risk of detonation or deflagration within a reaction vessel for the OCM process may increase.

The methane-to-oxygen stoichiometric ratio may be greater than about 2:1; greater than about 2.25:1; greater than about 2.5:1; greater than about 2.75:1; greater than about 3:1; greater than about 3.5:1; greater than about 4:1; greater than about 4.5:1; greater than about 5:1; greater than about 7.5:1; or greater than about 10:1. As a specific example, the stoichiometric ratio of methane to oxygen is about 5:1.

The methane feed and oxidant may be combined or introduced concurrently to the catalyst. The composition of the methane feed and oxidant as oxygen mixture may provide an additional variable in controlling the OCM process. The amount of oxygen feed delivered to the oxidative conversion process and present throughout the reaction system may dictate the process yield. The conversion of methane in the OCM process can also be affected or influenced by the overall composition of the methane feed and/or oxygen concentration as exposed to the catalyst. In various instances, one or more inert gases such as nitrogen may be present in the methane/oxygen mixture. The presence of inert gases may provide a stable thermal "heat sink" within the methane and oxygen OCM reactant mixture that is capable of absorbing thermal energy and consequently limits the temperature increase experienced by the oxygen, methane and OCM gas present at the catalyst. Thus the ratio of methane to oxygen (for example, the stoichiometric ratio of methane to oxygen) within the methane/oxygen mixture may affect the overall conversion of methane in the OCM reaction.

As provided herein, the methane and oxidant which may combine to form the OCM reactant mixture may include other gases such as longer chain, alkane, alkene, and alkyne hydrocarbons. In at least some instances, the methane source or the oxidant may contain one or more inert gases such as nitrogen. Thus, by controlling the quantity of methane or inert gas present in the methane source and controlling the quantity of oxygen or inert gas present in the oxidant, a methane/oxygen mixture having virtually any composition and methane to oxygen stoichiometric ratio can be provided.

According to the methods and processes described herein, the oxidative coupling of methane may include the reaction of methane and an oxidant, such as oxygen, in the presence of at least one suitable catalyst. In further aspects the catalyst is an active OCM catalyst. The exact elemental components or morphological form of the catalysts is not critical, provided they may be used in combination with the supports, diluents and/or binders described herein. For any of the active catalysts described herein, the catalyst may comprise a $C_{2+}$ selectivity of greater than 50% and a methane conversion of greater than 20% when the catalyst is employed as a heterogeneous catalyst in the oxidative coupling of methane at a temperature of 750° C. or less. In certain aspects, the foregoing catalysts may comprise a C2 selectivity of greater than 50% and a methane conversion of greater than 10%, 15%, 20% or even 25% when the catalyst is employed as a heterogeneous catalyst in the oxidative coupling of methane at a temperature of 750° C. or less.

A catalyst used according to the processes described herein may provide a C2 (as well as compounds with more than two carbons) selectivity of greater than 50%, greater than 55%, greater than 60%, greater than 65%, greater than 70%, or greater than 75%. The catalysts may provide a methane conversion of greater than 10%, greater than 12%, greater than 15%, greater than 20%, greater than 22%, greater than 25%, and even greater than 30%. In certain aspects, the catalysts may provide selectivity of 50% or greater with conversion of greater than 10%, greater than 15%, greater than 20%, greater than 25%, or greater than 30%. Likewise, in still further aspects, the catalysts may provide a selectivity of 55% or greater with conversion of greater than 10%, greater than 15%, greater than 20%, greater than 25%, or greater than 30%.

Various systems may make use of the integrated processes and methods described herein. A method of converting a methane feedstock or feedstream may comprise subjecting a methane feedstock or feedstream with an oxidant in the presence of a suitable catalyst at a certain temperature and pressure to facilitate an oxidative coupling reaction. The method may further comprises separating at least a portion of products from the OCM product mixture and re-directing a remaining portion of the product mixture to the methane feedstock and oxidant for oxidative conversion.

In the present description, certain specific details are set forth in order to provide a thorough understanding of various embodiments. However, one skilled in the art will understand that the disclosure may be practiced without these details. In other instances, well-known structures, standard vessel design details, details concerning the design and construction of pressure vessels, and the like have not been shown or described in detail to avoid unnecessarily obscuring descriptions of the disclosure.

Instrumentation, such as sensors, transmitters, and the like, and controls, such as single or multi-loop controllers, programmable logic controllers, and distributed control systems, suitable for the measurement and control of gas (for example, methane, oxygen, nitrogen, ethane, ethylene, etc.) composition and concentration, temperature, pressure are well known in the art are noted, but are not detailed herein for brevity.

While aspects of the present disclosure can be described and claimed in a particular statutory class, such as the system statutory class, this is for convenience only and one of skill in the art will understand that each aspect of the present disclosure can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Aspects

The present disclosure comprises at least the following aspects.

Aspect 1. A reactor system for an oxidative conversion of methane, the reactor system comprising: a reactor vessel having a reactant inlet and a product outlet; a pre-heating component disposed within the reactor vessel configured to receive feedstock from the reactant inlet; and one or more reactor bodies configured to receive the feedstock from the reactant inlet via the pre-heating component, each reactor body having a plurality of channels extending there through, wherein the channels are configured to receive a catalyst.

Aspect 1B. A reactor system for an oxidative conversion of methane, the reactor system consisting essentially of: a reactor vessel having a reactant inlet and a product outlet; a pre-heating component disposed within the reactor vessel configured to receive feedstock from the reactant inlet; and one or more reactor bodies configured to receive the feedstock from the reactant inlet via the pre-heating component, each reactor body having a plurality of channels extending there through, wherein the channels are configured to receive a catalyst.

Aspect 1C. A reactor system for an oxidative conversion of methane consisting of: a reactor vessel having a reactant inlet and a product outlet; a pre-heating component disposed within the reactor vessel configured to receive feedstock from the reactant inlet; and one or more reactor bodies configured to receive the feedstock from the reactant inlet via the pre-heating component, each reactor body having a plurality of channels extending there through, wherein the channels are configured to receive a catalyst.

Aspect 2. A reactor system for an oxidative conversion of methane, the reactor system comprising: a reactor vessel having a reactant inlet and a product outlet; a pre-heating component disposed within the reactor vessel configured to receive feedstock from the reactant inlet; one or more reactor bodies configured to receive the feedstock from the reactant inlet via the pre-heating component, each reactor body having a plurality of channels extending there through, wherein the channels extend through from a first surface of a reactor body of the one or more reactor bodies to a second surface of the reactor body, wherein the channels are configured to receive a catalyst, wherein the channels have a diameter, and wherein the catalyst has a particle size of from about $1/4^{th}$ to about $1/20^{th}$ the size of the diameter of a channel; and one or more walls disposed adjacent one or more of the first surface and the second surface, wherein the walls are configured to maintain the catalyst within the channels.

Aspect 2B. A reactor system for an oxidative conversion of methane, the reactor system consisting essentially of: a reactor vessel having a reactant inlet and a product outlet; a pre-heating component disposed within the reactor vessel configured to receive feedstock from the reactant inlet; one or more reactor bodies configured to receive the feedstock from the reactant inlet via the pre-heating component, each reactor body having a plurality of channels extending there through, wherein the channels extend through from a first surface of a reactor body of the one or more reactor bodies to a second surface of the reactor body, wherein the channels are configured to receive a catalyst, wherein the channels have a diameter, and wherein the catalyst has a particle size of from about $1/4^{th}$ to about $1/20^{th}$ the size of the diameter of a channel; and one or more walls disposed adjacent one or more of the first surface and the second surface, wherein the walls are configured to maintain the catalyst within the channels.

Aspect 2C. A reactor system for an oxidative conversion of methane, the reactor system consisting of: a reactor vessel having a reactant inlet and a product outlet; a pre-heating component disposed within the reactor vessel configured to receive feedstock from the reactant inlet; one or more reactor bodies configured to receive the feedstock from the reactant inlet via the pre-heating component, each reactor body having a plurality of channels extending there through, wherein the channels extend through from a first surface of a reactor body of the one or more reactor bodies to a second surface of the reactor body, wherein the channels are configured to receive a catalyst, wherein the channels have a diameter, and wherein the catalyst has a particle size of from about $1/4^{th}$ to about $1/20^{th}$ the size of the diameter of a channel; and one or more walls disposed adjacent one or more of the first surface and the second surface, wherein the walls are configured to maintain the catalyst within the channels.

Aspect 3. The reactor system of any of aspects 1A-2, wherein the pre-heating component comprises a high heat conductive medium.

Aspect 4. The reactor system of any one of aspects 1A-3, wherein the plurality of channels extend in parallel and are conterminous.

Aspect 5. The reactor system of any of one aspects 1A-4, wherein the reactor bodies have a cylindrical shape and have a diameter of about 20 mm or greater.

Aspect 6. The reactor system of any one of aspects 1A-5, wherein, a channel of the plurality of channels has a length no greater than 300 mm.

Aspect 7. The reactor system of any one of aspects 1A-6, wherein a channel of the plurality of channels has a diameter of less than about 10 mm.

Aspect 8. The reactor system of any one of aspects 1A-7, wherein a channel of the plurality of channels has a diameter of about 5 mm.

Aspect 9. The reactor system of any one of aspects 1A-8, wherein the reactor body comprises an inert material having a thermal conductivity of at least about 2 Watts per meter Kelvin.

Aspect 10. The reactor system of any one of aspects 1A-9, wherein the channel is tubular.

Aspect 11. The reactor system of any one aspect of aspects 1A-10, wherein the reactor system is configured for an oxidative coupling of methane.

Aspect 12. The reactor system of any one of aspects 1A-11, wherein the reactor vessel comprises an inert material.

Aspect 13. The reactor system of any of aspects 1A-12, wherein the catalyst is an active catalyst from 500° C. to 1200° C.

Aspect 14. The reactor system of any one of aspects 1A-13, wherein the catalyst has a particle size less than about 100 mesh.

Aspect 15. The reactor system of any one of aspects 1A-14, wherein the catalyst has a particle size of from about 20 mesh to about 80 mesh.

Aspect 16. The reactor system of any one of aspects 1A-14, wherein the catalyst has a particle size of from about 35 mesh to about 50 mesh.

Aspect 17. The reactor system of any one of aspects 1A-16, wherein the pre-heating component comprises a high heat conductive inert medium in the form spheres, cylinders, hollow cylinders or other shapes.

Aspect 18. The reactor system of aspect 17, wherein the high heat conductive inert medium comprises a silicon carbide, quartz, a metal coated with inert materials, or a combination thereof.

Aspect 19. The reactor system of any one of aspects 1A-18, wherein the reactor vessel comprises a refractory material.

Aspect 20. The reactor system of any one of aspects 1A-18, wherein the reactor vessel comprises alumina, silica, stainless steel, or zirconia.

Aspect 21A. A fixed bed reactor comprising: a reactor body having a plurality of channels extending there through, wherein the channels extend through from a first surface of the reactor body to a second surface of the reactor body, wherein the channels are about parallel to one another, and wherein the channel has a diameter of less than about 10 mm, wherein the channels are configured to receive a catalyst, wherein the catalyst has a particle size less than about $\frac{1}{10}$th the diameter of the a channel; and one or more walls disposed adjacent the first surface and the second surface configured to maintain the catalyst within the channels.

Aspect 21B. A fixed bed reactor consisting essentially of: a reactor body having a plurality of channels extending there through, wherein the channels extend through from a first surface of the reactor body to a second surface of the reactor body, wherein the channels are about parallel to one another, and wherein the channel has a diameter of less than about 10 mm, wherein the channels are configured to receive a catalyst, wherein the catalyst has a particle size less than about $\frac{1}{10}^{th}$ the diameter of the a channel; and one or more walls disposed adjacent the first surface and the second surface configured to maintain the catalyst within the channels.

Aspect 21C. A fixed bed reactor consisting of: a reactor body having a plurality of channels extending there through, wherein the channels extend through from a first surface of the reactor body to a second surface of the reactor body, wherein the channels are about parallel to one another, and wherein the channel has a diameter of less than about 10 mm, wherein the channels are configured to receive a catalyst, wherein the catalyst has a particle size less than about $\frac{1}{10}^{th}$ the diameter of the a channel; and one or more walls disposed adjacent the first surface and the second surface configured to maintain the catalyst within the channels.

Aspect 22. A method for converting a hydrocarbon feedstock to coupled hydrocarbon products, the method comprising: contacting the hydrocarbon feedstock and an oxidant with a catalyst in a reactor system, wherein the reactor system comprises: a reaction vessel having at least a reactant inlet and at least a product outlet; one or more reactor bodies configured to receive the hydrocarbon feedstock and oxidant from the reactant inlet, each reactor body having a plurality of channels extending there through, wherein the channels extend through from a first surface of the reactor body to a second surface of the reactor body, wherein the reactor body has a height up to about 300 mm, and a diameter of about 20 mm or greater, wherein the channels are configured to receive the catalyst, wherein the channels have a diameter of less than 10 mm, and wherein the catalyst has a particle size about $\frac{1}{10}^{th}$ the size of the diameter of a channel; and one or more walls disposed adjacent one or more of the first surface and the second surface, wherein the walls are configured to maintain the catalyst within the channels, at reaction conditions to provide a $C_{2+}$ hydrocarbon reaction product.

Aspect 22B. A method for converting a hydrocarbon feedstock to coupled hydrocarbon products, the method consisting of: contacting the hydrocarbon feedstock and an oxidant with a catalyst in a reactor system, wherein the reactor system comprises: a reaction vessel having at least a reactant inlet and at least a product outlet; one or more reactor bodies configured to receive the hydrocarbon feedstock and oxidant from the reactant inlet, each reactor body having a plurality of channels extending there through, wherein the channels extend through from a first surface of the reactor body to a second surface of the reactor body, wherein the reactor body has a height up to about 300 mm, and a diameter of about 20 mm or greater, wherein the channels are configured to receive the catalyst, wherein the channels have a diameter of less than 10 mm, and wherein the catalyst has a particle size about $\frac{1}{10}^{th}$ the size of the diameter of a channel; and one or more walls disposed adjacent one or more of the first surface and the second surface, wherein the walls are configured to maintain the catalyst within the channels, at reaction conditions to provide a $C_{2+}$ hydrocarbon reaction product.

Aspect 22C. A method for converting a hydrocarbon feedstock to coupled hydrocarbon products, the method consisting essentially of: contacting the hydrocarbon feedstock and an oxidant with a catalyst in a reactor system, wherein the reactor system comprises: a reaction vessel having at least a reactant inlet and at least a product outlet; one or more reactor bodies configured to receive the hydrocarbon feedstock and oxidant from the reactant inlet, each reactor body having a plurality of channels extending there through, wherein the channels extend through from a first surface of the reactor body to a second surface of the reactor body, wherein the reactor body has a height up to about 300 mm, and a diameter of about 20 mm or greater, wherein the channels are configured to receive the catalyst, wherein the channels have a diameter of less than 10 mm, and wherein the catalyst has a particle size about $\frac{1}{10}^{th}$ the size of the diameter of a channel; and one or more walls disposed adjacent one or more of the first surface and the second surface, wherein the walls are configured to maintain the catalyst within the channels, at reaction conditions to provide a $C_{2+}$ hydrocarbon reaction product.

Aspect 23A. A reactor system for an oxidative conversion of methane, the reactor system comprising: a reactor vessel having a reactant inlet and a product outlet; a pre-heating component disposed within the reactor vessel configured to receive feedstock from the reactant inlet; one or more reactor bodies configured to receive the feedstock from the reactant inlet via the pre-heating component, each reactor body having a plurality of channels extending there through, wherein the channels extend through from a first surface of a reactor body of the one or more reactor bodies to a second surface of the reactor body, wherein the channels are configured to receive a catalyst, wherein the channels have a diameter, and wherein the catalyst has a particle size of from about 20 mesh to about 80 mesh; wherein the reactor body has a height no greater than 300 mm.

Aspect 23B. A reactor system for an oxidative conversion of methane, the reactor system consisting essentially of: a reactor vessel having a reactant inlet and a product outlet; a pre-heating component disposed within the reactor vessel configured to receive feedstock from the reactant inlet; one or more reactor bodies configured to receive the feedstock from the reactant inlet via the pre-heating component, each reactor body having a plurality of channels extending there through, wherein the channels extend through from a first surface of a reactor body of the one or more reactor bodies to a second surface of the reactor body, wherein the channels are configured to receive a catalyst, wherein the channels have a diameter, and wherein the catalyst has a particle size of from about 20 mesh to about 80 mesh; wherein the reactor body has a height no greater than 300 mm.

Aspect 23C. A reactor system for an oxidative conversion of methane, the reactor system consisting of: a reactor vessel having a reactant inlet and a product outlet; a pre-heating component disposed within the reactor vessel configured to receive feedstock from the reactant inlet; one or more reactor bodies configured to receive the feedstock from the reactant inlet via the pre-heating component, each reactor body having a plurality of channels extending there through, wherein the channels extend through from a first surface of a reactor body of the one or more reactor bodies to a second surface of the reactor body, wherein the channels are configured to receive a catalyst, wherein the channels have a diameter, and wherein the catalyst has a particle size of from about 20 mesh to about 80 mesh; wherein the reactor body has a height no greater than 300 mm.

Aspect 24. A reactor system for an oxidative conversion of methane, the reactor system comprising: a reactor vessel having a reactant inlet and a product outlet; a pre-heating component disposed within the reactor vessel configured to receive feedstock from the reactant inlet; one or more reactor bodies configured to receive the feedstock from the reactant inlet via the pre-heating component, wherein the pre-heating component comprises a high heat conductive inert medium, wherein each reactor body having a plurality of channels extending there through, wherein the channels extend through from a first surface of a reactor body of the one or more reactor bodies to a second surface of the reactor body, wherein the channels are configured to receive a catalyst, wherein the channels have a diameter, and wherein the catalyst has a particle size of from about 20 mesh to about 80 mesh, and wherein the reactor body has a height no greater than 300 mm.

Aspect 24B. A reactor system for an oxidative conversion of methane, the reactor system consisting essentially of: a reactor vessel having a reactant inlet and a product outlet; a pre-heating component disposed within the reactor vessel configured to receive feedstock from the reactant inlet; one or more reactor bodies configured to receive the feedstock from the reactant inlet via the pre-heating component, wherein the pre-heating component comprises a high heat conductive inert medium, wherein each reactor body having a plurality of channels extending there through, wherein the channels extend through from a first surface of a reactor body of the one or more reactor bodies to a second surface of the reactor body, wherein the channels are configured to receive a catalyst, wherein the channels have a diameter, and wherein the catalyst has a particle size of from about 20 mesh to about 80 mesh, and wherein the reactor body has a height no greater than 300 mm.

Aspect 24C. A reactor system for an oxidative conversion of methane, the reactor system consisting of: a reactor vessel having a reactant inlet and a product outlet; a pre-heating component disposed within the reactor vessel configured to receive feedstock from the reactant inlet; one or more reactor bodies configured to receive the feedstock from the reactant inlet via the pre-heating component, wherein the pre-heating component comprises a high heat conductive inert medium, wherein each reactor body having a plurality of channels extending there through, wherein the channels extend through from a first surface of a reactor body of the one or more reactor bodies to a second surface of the reactor body, wherein the channels are configured to receive a catalyst, wherein the channels have a diameter, and wherein the catalyst has a particle size of from about 20 mesh to about 80 mesh, and wherein the reactor body has a height no greater than 300 mm.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (for example, amounts, temperature, etc.), but some errors and deviations should be accounted for.

There are numerous variations and combinations of reaction conditions, for example, component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Two catalyst samples (Examples 1 and 2) were prepared to demonstrate the effect of catalyst particle size. For Example 1, 1.74 grams (g) of manganese(II) nitrate tetrahydrate $Mn(NO_3)_2.4H_2O$ is dissolved into 15 ml de-ionized water, which is then added into 28.6 g of silica sol (Nalco 1034A) having a silica content of 34%. A mass of 1.12 g of sodium tungstate dihydrate $(Na_2WO_4.2H_2O)$ was dissolved in 10 ml de-ionized water and then added into the above mixture. An additional 50 ml deionized water was added to the mixture. The mixture obtained was agitated for 2 hours at 90° C. The agitated mixture was then dried at 120° C. for 12 hours. The resulting material is sized from about 50 to 35 mesh particle size (0.297 mm to 0.425 mm). The particles were subjected to calcination at 800° C. for 6 hours to form the desired catalyst. The catalyst was performance tested in a quartz reactor with 4 mm internal diameter with 100 milligram (mg) loading. The reactor was heated to the desired temperature, and a mixture of methane and oxygen at a fixed $CH_4:O_2$ ratio of 7.4 was fed to the reactor at a total flow rate of 33.3 standard cubic centimeters per minute (sccm).

In Example 2, the same catalyst as Example 1 was made except with a larger particle size of 2 to 3 mm. The catalyst obtained was performance tested in a quartz reactor with a 22 mm internal diameter with 5.0 g loading. The reactor was heated to the required temperature, and a mixture of methane and oxygen at a fixed $CH_4: O_2$ ratio of 7.4 was fed to the reactor at a total flow rate of 282.1 sccm. The results obtained are shown in Table 1.

TABLE 1

Conversion and selectivity for Examples 1 and 2.

| Catalyst Example | Particle size | Reactor diameter | Temp (° C.) | $CH_4$ Conv. (%) | $O_2$ Conv. (%) | $C_{2+}$ sel. (%) | $C_{2+}$ prod. (mmol/g-Cat/hr) | Scale-up effectiveness factor (%) |
|---|---|---|---|---|---|---|---|---|
| 1 | 35-50 mesh | 4 mm | 775 | 18.8 | 95.3 | 78.3 | 115.5 | — |
| 2 | 2-3 mm | 22 mm | 750 | 17.2 | 95.8 | 70.2 | 16.1 | 13.9 |

Comparing the results of Examples 1 and 2, it can be seen that when a larger catalyst particle is used and the reaction is carried out with a larger reactor diameter and with higher flowrate, a lower product selectivity was obtained. With larger catalyst particle size, there is enhanced mass and heat transfer resistance within the catalyst particles. For the reactor with a larger tube diameter (22 mm as in Example 2), there were higher mass and heat transfer resistance observed within the reactor compared to the 4 mm diameter reactor. With a higher feed rate, more reaction heat is generated resulting in a higher hot spot temperature in the reactor. With these resistances, the productivity of $C_{2+}$ products (mmol/g-cat/hr) obtained with the larger scale operation is significantly lower, its scale-up effectiveness factor is only 13.9%. The ratio of the productivity from scale-up operation to that of the small scale operation is defined as the scale-up effectiveness factor.

Examples 3 and 4 were prepared to demonstrate the influence of size of the reactor and catalyst particle size. Example 3 included a $Sr_{1.0}Ce_{0.9}Yb_{0.1}O_x$ catalyst formed by mixing 4.23 g of strontium nitrate $Sr(NO_3)_2$, 7.82 g of cerium(III) nitrate hexahydrate $Ce(NO_3)_3 \cdot 6H_2O$, and 0.90 g of ytterbium(III) nitrate pentahydrate $Yb(NO_3)_3 \cdot 5H_2O$ and dissolving the mixture into 25 ml of water. The mixture obtained was dried at 125° C. overnight. The dried material was then calcined at 900° C. for 6 hours to get yield the catalyst. For small scale testing, the catalyst obtained was sized between 35 and 50 mesh, and the sized catalyst was tested in a quartz reactor with a 2.3 mm internal diameter with a catalyst loading of 20 mg. The reactor was heated to the required temperature and a mixture of methane and oxygen at a fixed $CH_4:O_2$ ratio of 16.0 was fed to the reactor at a total flow rate of 40.0 sccm. The performance obtained under this condition is shown in Table 2.

For larger scale testing, which is Example 4, the dried material of Example 3 was formed into cylindrical tablets having a diameter of 2 mm and height 2.3 mm and the tablets were calcined. A mass of 1.85 g of the tablets were loaded into a 13 mm internal diameter quartz tube and the performance data were obtained under a total flow rate of 927.0 sccm with methane and oxygen at a fixed $CH_4:O_2$ ratio of 16.0. Table 2 presents the performance observed.

Comparing the results of Examples 3 and 4, a larger catalyst particle with a larger reactor diameter and higher flowrate provided a much lower product selectivity. These results were consistent with that obtained in Example 2. With a larger catalyst particle size, there will be enhanced mass and heat transfer resistance within the catalyst particle. With the reactor with larger tube diameter, there is a higher mass and heat transfer resistance within the reactor compared to the 2.3 mm internal diameter reactor. With higher feed rate, more reaction heat is generated which results in a higher hot spot temperature and, thus, a non-uniform temperature profile in the reactor. All these conditions result in a much lower catalyst productivity when it is used in scaled-up operation as shown by Example 4, the scale-up effectiveness factor is only 12.0%.

Figure 4:
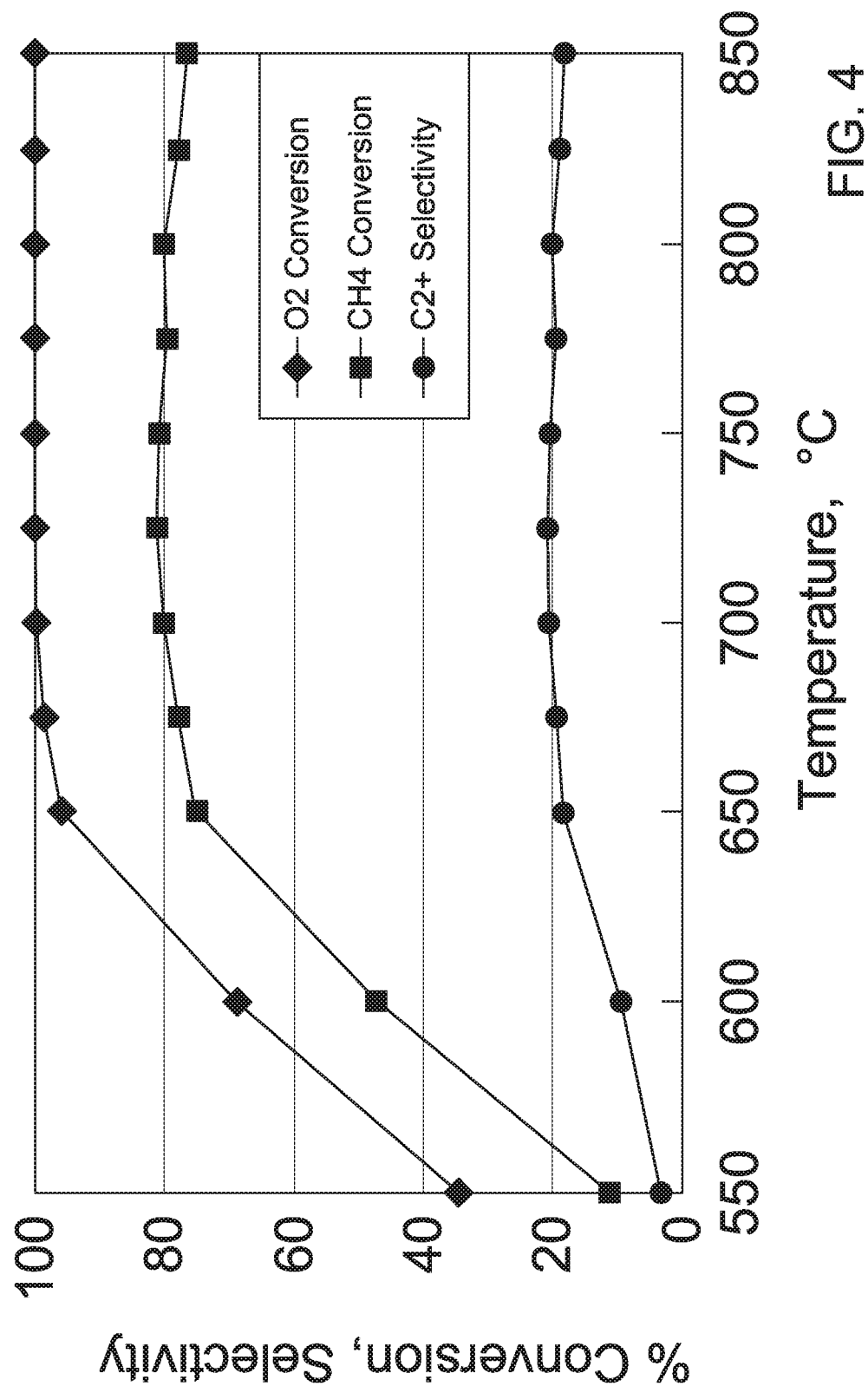
FIG. 4 shows the performance of the catalyst in Example 5.

Example 5 is another example of small scale operation. It included a $Sr_{1.0}La_{0.9}Nd_{0.7}Yb_{0.10}O_x$ catalyst formed by mixing 10.58 g of $Sr(NO_3)_2$, 19.48 g of lanthanum(III)nitrate hexahydrate $La(NO_3)_3 \cdot 6H_2O$, 15.35 g of neodymium nitrate hexahydrate $Nd(NO_3)_3 \cdot 6H_2O$ and 2.26 g of $Yb(NO_3)_3 \cdot 5H_2O$ and dissolving the mixture into 100 ml of water. The mixture obtained was dried at 125° C. overnight. The dried material was then calcined at 900° C. for 6 hours to get yield the catalyst. The catalyst obtained was sized between 35 and 50 mesh, and the sized catalyst was performance tested in a quartz reactor with a 2.3 mm internal diameter with a catalyst loading of 20 mg. The reactor was heated to the required temperature and a mixture of methane and oxygen at a fixed $CH_4:O_2$ ratio of 7.4 was fed to the reactor at a total flow rate of 40.0 sccm. The $O_2$ conversions, $C_{2+}$ selectivities and $CH_4$ conversions obtained under different reactor temperatures are shown in FIG. 4. The performance obtained at 675° C. is shown in Table 3. The productivity for $C_{2+}$ obtained under this condition is 782.4 mmol/g-cat/hr.

Example 6 is a larger scale operation, and it was carried out by loading the catalyst obtained in Example 5 into a SiC monolith with outside diameter of 26 mm. As shown in FIG. 3, the monolith has 60 cells with each cell having the dimension of 2 mm by 2 mm. 28 cells of the 60 cells are loaded with catalyst with 20 mg in each cell, the total catalyst loading of 0.58 g. The rest cells were blocked. The monolith was then loaded into a quartz lube reactor with

TABLE 2

Conversion and selectivity for Examples 3 and 4.

| Catalyst Example | Reactor internal diameter (mm) | Particle Size | Temp. (° C.) | $CH_4$ Conv. (%) | $O_2$ Conv. (%) | $C_{2+}$ sel. (%) | $C_{2+}$ prod. (mmol/g-Cat/hr) | Scale-up effectiveness factor (%) |
|---|---|---|---|---|---|---|---|---|
| 3 | 2.3 | 35-50 Mesh | 775 | 12.0 | 99.0 | 88.1 | 533.1 | — |
| 4 | 13 | ~2 × 2.3 mm tablets | 750 | 10.7 | 74.4 | 47.4 | 64.1 | 12.0 | inner diameter of 33 mm. The gap between the monolith and the quartz tube was sealed. The monolith was tested under a total flowrate of 2176 sccm with $CH_4$ to $O_2$ ratio of 16. The performance obtained was shown in Table 3.

With the same catalyst loading, the test (Example 7) was carried again at a total flowrate of 3264 with $CH_4$ to $O_2$ ratio of 16 and the performance was shown in Table 3 as well.

The scale-up effectiveness factors for Examples 6 and 7 are 65.2% and 93.5% respectively. It can be seen from Examples 6 and 7 that the productivities and effectiveness factor obtained with the packed monolith structure are very high, and are much higher than that obtained from Examples 2 and 4, indicating that the novel packed monolith reactor sustains the intrinsic catalyst performance much better than the traditional scale-up method.

Example 8 was carried out by loading the catalyst obtained in Example 5 into a SiC monolith with outside diameter of 26 mm as Examples 6 and 7. In this example, all the 60 cells were loaded with catalyst with 20 mg of catalyst in each cell, the total catalyst loading is 1.20 g. The monolith was then loaded into a quartz lube reactor with inner diameter of 33 mm. The gap between the monolith and the quartz tube was sealed. The monolith was tested under a total flowrate of 2176 sccm with $CH_4$ to $O_2$ ratio of 16. The performance obtained was shown in Table 3. The monolith was tested again (Example 9) under a total flowrate of 3264 sccm with $CH_4$ to $O_2$ ratio of 8.5. The performance obtained was shown in Table 3 as well.

It can be seen that the $CH_4$ conversion and $O_2$ conversion were improved with more catalyst loaded compared to Examples 6 and 7.

The effectiveness factors obtained from Examples 8 and 9 are 42.7% and 68.0% respectively, both are much higher than that obtained from Examples 2 and 4. These two examples demonstrated again that the novel packed monolith reactor sustains the intrinsic catalyst performance much better than the traditional scale-up method.

TABLE 3

Conversion selectivity and productivity for Examples 5, 6, 7, 8 and 9.

| Catalyst Example | Reactor internal diameter (mm) | Particle Size (MESH) | Temp. (° C.) | $CH_4$ Conv. (%) | $O_2$ Conv. (%) | $C_{2+}$ sel. (%) | $C_{2+}$ prod. (mmol/g – Cat/hr) | Scale-up effectiveness factor (%) |
|---|---|---|---|---|---|---|---|---|
| 5 | 2.3 | 35-50 | 725 | 20.7 | 100.0 | 81.1 | 782.4 | — |
| 6 | 2 * 2 * 28 | 35-50 | 725 | 7.1 | 64.4 | 76.8 | 510.6 | 65.2 |
| 7 | 2 * 2 * 28 | 35-50 | 750 | 6.7 | 60.0 | 77.7 | 731.2 | 93.5 |
| 8 | 2 * 2 * 60 | 35-50 | 700 | 9.5 | 88.5 | 76.7 | 333.8 | 42.7 |
| 9 | 2 * 2 * 60 | 35-50 | 725 | 12.5 | 76.7 | 65.3 | 532.2 | 68.0 |

The above description is intended to be illustrative, and not restrictive. For example, the above-described examples (or one or more aspects thereof) may be used in combination with each other. Other aspects can be used, such as by one of ordinary skill in the art upon reviewing the above description. The Abstract is provided with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed aspect. Thus, the following claims are hereby incorporated into the Detailed Description as examples or aspects, with each claim standing on its own as a separate aspect, and it is contemplated that such aspects can be combined with each other in various combinations or permutations. The scope of the disclosure should be determined with reference to the appended claims, along with the full scope of equivalents to which such claims are entitled.

Definitions

It is to be understood that the terminology used herein is for the purpose of describing particular aspects only and is not intended to be limiting. As used in the specification and in the claims, the term "comprising" can include the embodiments "consisting of" and "consisting essentially of" Unless defined otherwise, all technical and scientific terms used herein have the same meaning as commonly understood by one of ordinary skill in the art to which this disclosure belongs. In this specification and in the claims which follow, reference will be made to a number of terms which shall be defined herein.

As used in the specification and the appended claims, the singular forms "a," "an" and "the" include plural equivalents unless the context clearly dictates otherwise. Thus, for example, reference to "a polycarbonate polymer" includes mixtures of two or more polycarbonate polymers.

As used herein, the term "combination" is inclusive of blends, mixtures, alloys, reaction products, and the like.

As used herein, the term "heat transfer efficiency" may refer to how well a reactor system, such as a fixed bed reactor system, exchanges heat.

Ranges can be expressed herein as from one particular value to another particular value. When such a range is expressed, another aspect includes from the one particular value and/or to the other particular value. Similarly, when values are expressed as approximations, by use of the antecedent 'about,' it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "about" and "at or about" mean that the amount or value in question can be the value designated some other value approximately or about the same. It is generally understood, as used herein, that it is the nominal value indicated ±5% variation unless otherwise indicated or inferred. The term is intended to convey that similar values promote equivalent results or effects recited in the claims. That is, it is understood that amounts, sizes, formulations, parameters, and other quantities and characteristics are not and need not be exact, but can be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. It is understood that where "about" is used before a quantitative value, the parameter also includes the specific quantitative value itself, unless specifically stated otherwise.

Disclosed are the components to be used to prepare the compositions of the disclosure as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the disclosure. Thus, if there are a variety of additional steps that can be performed it is understood that each of these additional steps can be performed with any specific aspect or combination of aspects of the methods of the disclosure.

The term "OCM process," as used herein, generally refers to a process that employs or substantially employs an oxidative coupling of methane (OCM) reaction. An OCM reaction can include the oxidation of methane to a hydrocarbon and water, and involves an exothermic reaction. In an OCM reaction, methane can be partially oxidized to one or more $C_{2+}$ compounds, such as ethylene. In an example, an OCM reaction is $2CH_4 + O_2 \rightarrow C_2H_4 + 2H_2O$. An OCM reaction can yield $C_{2+}$ compounds. An OCM reaction can be facilitated by a catalyst, such as a heterogeneous catalyst. Additional by-products of OCM reactions can include CO, $CO_2$, $H_2$, as well as hydrocarbons, such as, for example, ethane, propane, propene, butane, butane, and the like.

The term "non-OCM process," as used herein, generally refers to a process that does not employ or substantially employ an oxidative coupling of methane reaction. Examples of processes that may be non-OCM processes include non-OCM hydrocarbon processes, such as, for example, non-OCM processes employed in hydrocarbon processing in oil refineries, a natural gas liquids separations processes, steam cracking of ethane, Fischer-Tropsch processes, among others.

The terms "$C_{2+}$," and "$C_{2+}$ compound," as used herein, generally refer to a compound comprising two or more carbon atoms, for example, C2, C3, etc. $C_{2+}$ compounds include, without limitation, alkanes, alkene, alkynes, aldehydes, ketones, aromatics esters and carboxylic acids containing two or more carbon atoms. Examples of $C_{2+}$ compounds include ethane, ethene, ethyne, propane, propene and propyne, etc.

The term "non-$C_{2+}$ impurities," as used herein, generally refers to material that does not include $C_{2+}$ compounds. Examples of non-$C_{2+}$ impurities, which may be found in certain OCM reaction product streams, include nitrogen (N2), oxygen (O2), water (H20), argon (Ar), hydrogen (H2) carbon monoxide (CO), carbon dioxide (CO2) and methane (CH4).

The term "methane conversion," as used herein, generally refers to the percentage or fraction of methane introduced into the reaction that is converted to a product other than methane. The term "$C_{2+}$ selectivity," as used herein, generally refers to the percentage of all carbon containing products of an oxidative coupling of methane ("OCM") reaction that are the desired or otherwise preferable $C_{2+}$ products, for example, ethane, ethylene, propane, propylene, etc. Although primarily stated as $C_{2+}$ selectivity, it will be appreciated that selectivity may be stated in terms of any of the desired products, for example, just C2, or just C2 and C3.

The term "$C_{2+}$ yield," as used herein, generally refers to the amount of carbon that is incorporated into a $C_{2+}$ product as a percentage of the amount of carbon introduced into a reactor in the form of methane. This may generally be calculated as the product of the conversion and the selectivity divided by the number of carbon atoms in the desired product. $C_{2+}$ yield is typically additive of the yield of the different $C_{2+}$ components included in the $C_{2+}$ components identified, for example, ethane yield+ethylene yield+propane yield+propylene yield etc.).

As used herein the term "adiabatic" refers to a system experiencing minimal or ideally no interchange or exchange of thermal energy with the surrounding environment. As used herein "adiabatic" vessels and vessels said to be operating under "adiabatic" conditions refer to vessels having no provision specifically for the removal or addition of thermal energy to or from the system. Notwithstanding the foregoing, it will be appreciated that incidental thermal transfer between the vessel and its environment is contemplated within the context of the foregoing definition. Generally, where an adiabatic vessel is used to contain a reaction that releases thermal energy (i.e., an "exothermic" reaction), a positive temperature profile will be maintained between the reactants added to the vessel and the products removed from the vessel. In other words, the products removed from the vessel will generally be at a temperature above the temperature of the reactants introduced to the vessel since the thermal energy liberated by the reaction can only be substantially removed by the products of the reaction.

As used herein the term "stoichiometric ratio" refers to the ratio of one compound to another compound. For example in the OCM reaction, theoretically two moles of methane are required to react with one mole of oxygen, yielding a balanced stoichiometric ratio of 2:1. The actual concentration of methane to oxygen may be greater than or less than 2:1. For example, where the stoichiometric ratio is 1.5 moles of methane to 1 mole of oxygen (1.5:1), methane is considered the limiting reagent since an insufficient quantity of methane is present to consume all of the oxygen. Similarly, where the stoichiometric ratio is 3 moles of methane to 1 mole of oxygen (3:1), oxygen can be considered the limiting reagent since an insufficient quantity of oxygen is present to consume all of the methane.

As used herein the term "temperature profile" or "thermal profile" refers to the temperature as a function of position through a reactor system or portion of a reactor system. A temperature or thermal profile can be either a two-dimensional (for example, linear function of distance through a catalyst bed) or three dimensions (for example linear function of distance through a catalyst bed, to provide a thermal profile as a function of distance through the catalyst bed, and radial function of distance from the center of a catalyst bed, to provide a thermal profile as a function of distance from the center of the catalyst bed).

As used herein the term "gas hourly space velocity" or the acronym "GHSV" refers to the ratio of reactant gas flow rate (methane source+oxidant) in standard cubic feet per hour or standard cubic meters per hour, divided by the reactor volume (cubic feet or cubic meters). Where diluent gases are added, the GHSV includes the additional volume presented by the diluent gases. As used herein the term "velocity" refers to the superficial or linear velocity of a bulk gas flowing through a defined cross sectional area (for example SCFM or ACFM divided by the actual or equivalent cross sectional area in square feet). The resultant ratio has units of inverse hours and is used to relate reactant gas flow rate to reactor volume. The GHSV is one factor considered when scaling a known reactor design to accommodate a lesser or greater reactant flow.

As used herein the term "higher hydrocarbons" refers to any carbon compound containing at least two carbon atoms and includes alkane, alkene, alkynes, cycloalkanes, and aromatic hydrocarbons.

Unless otherwise stated to the contrary herein, any test standards described are the most recent standard in effect at the time of filing this application.

What is claimed is:

1. A reactor system for an oxidative conversion of methane comprising:
   a reactor vessel having a reactant inlet and a product outlet;
   a pre-heating component disposed within the reactor vessel configured to receive feedstock from the reactant inlet; and
   one or more reactor bodies configured to receive the feedstock from the reactant inlet via the pre-heating component, each reactor body having a plurality of channels extending from a first surface of the reactor body to a second surface of the reactor body, wherein the channels contain a catalyst, and one or more walls are disposed adjacent to one or more of the first surface and the second surface and are configured to maintain the catalyst within the plurality of channels.

2. The reactor system of claim 1, wherein the channels have a diameter, and wherein the catalyst has a particle size of from about $1/4^{th}$ to about $1/20^{th}$ the size of the diameter of a channel.

3. The reactor system of claim 1, wherein the plurality of channels extend in parallel and are conterminous.

4. The reactor system of claim 1, wherein the reactor bodies have a cylindrical shape and have a diameter of about 20 mm or greater.

5. The reactor system of claim 1, wherein at least one channel of the plurality of channels has a length no greater than 300 mm.

6. The reactor system of claim 1, wherein at least one channel of the plurality of channels has a diameter of less than about 10 mm.

7. The reactor system of claim 1, wherein at least one channel of the plurality of channels has a diameter of about 5 mm.

8. The reactor system of claim 1, wherein the reactor body comprises an inert material having a thermal conductivity of at least about 2 Watts per meter Kelvin.

9. The reactor system of claim 1, wherein the channel is tubular.

10. The reactor system of claim 1, wherein the reactor system is configured for an oxidative coupling of methane.

11. The reactor system of claim 1, wherein the reactor vessel comprises an inert material.

12. The reactor system of claim 1, wherein the catalyst is an active catalyst from 500° C. to 1200° C.

13. The reactor system of claim 1, wherein the reactor vessel comprises a refractory material.

14. A reactor system for an oxidative conversion of methane comprising:
   a reactor vessel having a reactant inlet and a product outlet;
   a pre-heating component disposed within the reactor vessel configured to receive a feedstock from the reactant inlet, wherein the pre-heating component comprises a silicon carbide, quartz, a metal coated with inert materials, or a combination thereof; and
   one or more reactor bodies configured to receive the feedstock from the reactant inlet via the pre-heating component, each reactor body having a plurality of channels extending there through and containing a catalyst.

15. A reactor system for an oxidative conversion of methane comprising:
   a reactor vessel having a reactant inlet and a product outlet;
   a pre-heating component disposed within the reactor vessel configured to receive a feedstock from the reactant inlet; and
   one or more reactor bodies configured to receive the feedstock from the reactant inlet via the pre-heating component, each reactor body having a plurality of channels extending there through and containing a catalyst with a particle size less than about 100 mesh.

16. The reactor system of claim 15, wherein the catalyst has a particle size of from about 20 mesh to about 80 mesh.

17. The reactor system of claim 15, wherein the catalyst has a particle size of from about 35 mesh to about 50 mesh.

* * * * *